(12) United States Patent
Lalleman

(10) Patent No.: US 8,518,126 B2
(45) Date of Patent: Aug. 27, 2013

(54) HAIR DYEING PROCESS USING A CHROMENE OR CHROMANE DYE

(75) Inventor: Boris Lalleman, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/391,604

(22) PCT Filed: Aug. 18, 2010

(86) PCT No.: PCT/EP2010/062047
§ 371 (c)(1),
(2), (4) Date: May 14, 2012

(87) PCT Pub. No.: WO2011/020857
PCT Pub. Date: Feb. 24, 2011

(65) Prior Publication Data
US 2012/0227190 A1    Sep. 13, 2012

Related U.S. Application Data

(60) Provisional application No. 61/242,118, filed on Sep. 14, 2009.

(30) Foreign Application Priority Data

Aug. 21, 2009 (FR) ..................................... 09 55728

(51) Int. Cl.
*A61Q 5/10* (2006.01)
(52) U.S. Cl.
USPC ................. 8/405; 8/407; 8/435; 8/576; 8/629

(58) Field of Classification Search
USPC .............................. 8/405, 407, 435, 576, 629
See application file for complete search history.

(56) References Cited

U.S. PATENT DOCUMENTS

| | | |
|---|---|---|
| 2004/0018996 A1 | 1/2004 | Richardson |
| 2007/0251024 A1 | 11/2007 | Greaves |
| 2010/0313362 A1 * | 12/2010 | Vainshelboim et al. .......... 8/425 |

FOREIGN PATENT DOCUMENTS

| | | |
|---|---|---|
| EP | 0 304 802 A2 | 3/1999 |
| EP | 1 915 981 A1 | 4/2008 |
| FR | 2 543 434 A1 | 10/1984 |
| FR | GB 2 190 104 A | 11/1987 |
| FR | 2 860 233 A1 | 4/2005 |
| GB | 2190 104 A * | 11/1987 |

OTHER PUBLICATIONS

STIC Search Report dated Jul. 27, 2012.*

* cited by examiner

*Primary Examiner* — Eisa Elhilo
(74) *Attorney, Agent, or Firm* — John A. Artz; Dickinson Wright PLLC

(57) ABSTRACT

The invention relates to a process for dyeing keratin fibers, such as human keratin fibers, and in particular the hair, comprising the application, to said fibers, of: i) a composition comprising one or more dyes chosen from chromene dyes and chromane dyes, ii) a composition comprising one or more zinc mineral salts, compositions i) and ii) being two distinct compositions or forming a single composition, said process excluding any use of a chemical oxidizing agent other than the oxygen in the air, and also to a composition and to the use thereof.

14 Claims, No Drawings

HAIR DYEING PROCESS USING A CHROMENE OR CHROMANE DYE

This application is a national phase application based on PCT/EP2010/062047 filed Aug. 18, 2010, which claims priority from French Application No. 0955728, filed Aug. 21, 2009, and claims the benefit of U.S. Provisional Application No. 61/242,118, filled on Sep. 14, 2009, the content of all of which is incorporated herein by reference in their entirety.

TECHNICAL FIELD

The subject of the invention is a process for dyeing keratin fibres comprising the application, to said fibres, of one or more dyes chosen from chromene dyes and chromane dyes and of one or more zinc mineral salts. The invention also relates to a composition comprising, inter alia, these compounds and to the use of said composition.

BACKGROUND

It is known practice to dye keratin fibres, and in particular human hair, with dye compositions containing oxidation dye precursors, generally known as oxidation bases, such as ortho- or para-phenylenediamines, ortho- or para-aminophenols and heterocyclic compounds. These oxidation bases are generally combined with couplers. These bases and these couplers are colourless or weakly coloured compounds which, when combined with oxidizing products, can give rise to coloured compounds via a process of oxidative condensation. This type of oxidizing dyeing makes it possible to obtain permanent colourings, but it causes a degradation of the keratin fibres owing to the use of oxidizing agents.

Moreover, it is known practice to dye keratin fibres, and in particular human hair, with dye compositions containing direct dyes. Conventional dyes which are used are in particular dyes of nitrobenzene, anthraquinone, nitropyridine, azo, xanthene, acridine, azine or triarylmethane type or natural dyes. These dyes are coloured or colouring molecules which have a certain affinity for keratin fibres.

The compositions containing one or more direct dyes are applied to the keratin fibres for a period of time necessary to obtain the desired colouration, and are then rinsed out. The resulting colourations are particularly chromatic colourations which are, however, temporary or semi-permanent since the nature of the interactions that bind the direct dyes to the keratin fibre, and their desorption from the surface and/or from the core of the fibre, are responsible for their poor dyeing power and their poor fastness with respect to washing or perspiration.

Nowadays, hair dyeing processes using natural products are increasingly appreciated by users.

It is known practice, from document FR 2 549 721, to use natural dyes for hair dyeing. However, the process described still remains to be improved in terms of efficiency.

There is therefore a real need to develop hair dyeing processes which result in powerful colourations which are relatively nonselective, which are resistant to external agents (light, bad weather, shampooing), and which respect the nature of the hair, using compositions containing natural dyes.

SUMMARY OF THE INVENTION

This objective is achieved by means of the present invention, the subject of which is a process for dyeing keratin fibres, such as human keratin fibres, and in particular the hair, comprising the application, to said fibres, of:

i) a composition comprising one or more dyes chosen from chromene dyes and chromane dyes, ii) a composition comprising one or more zinc mineral salts, compositions i) and ii) being two distinct compositions or forming a single composition, said process excluding any use of a chemical oxidizing agent other than the oxygen in the air.

A subject of the invention is also particular compositions combining one or more dyes chosen from chromene dyes and chromane dyes, one or more zinc mineral salts and one or more particular solvents.

Other characteristics, aspects and advantages of the present invention will emerge on reading the detailed description which follows.

DESCRIPTION OF THE PREFERRED EMBODIMENTS

The dyes used in the process according to the invention are dyes chosen from chromene dyes and chromane dyes.

According to the invention, the term "chromene or chromane dye" is intended to mean dyes which comprise, in their structure, at least one bicyclic compound of formula (A) below:

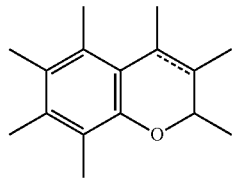

A the intracyclic bond ---- representing a carbon-carbon single bond or else a carbon-carbon double bond, as illustrated by formula A1 denoting the chromene family and formula A2 denoting the chromane family below:

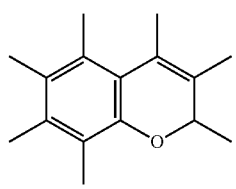

A1

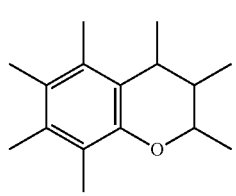

A2

More particularly, the dyes of formula (A) are chosen from the compounds having the following formulae:

formula (I), comprising, in its structure, the bicyclic compound of formula A2:

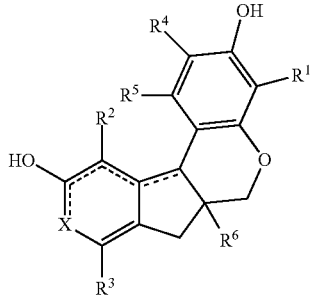

in which:
▱ represents a carbon-carbon single bond or a carbon-carbon double bond, the linking of these bonds ▱ denotes two carbon-carbon single bonds and two carbon-carbon double bonds, said bonds being conjugated, X represents a group:

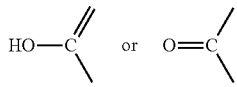

$R^1$, $R^2$, $R^3$, $R^4$, $R^5$ and $R^6$, which may be identical or different, represent, independently of one another, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof; and formula (II), comprising, in its structure, the bicyclic compound of formula A1:

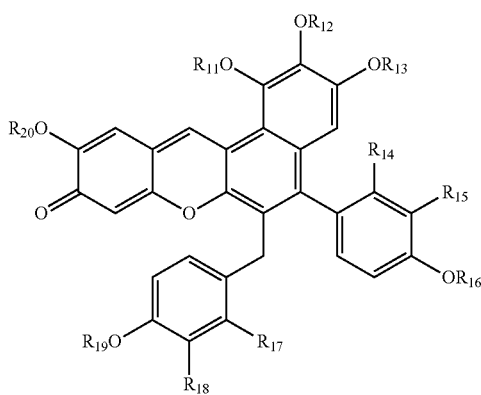

in which:
$R_{11}$, $R_{12}$, $R_{13}$, $R_{16}$, $R_{19}$ and $R_{20}$, which may be identical or different, represent, independently of one another, a hydrogen atom or a $C_1$-$C_4$ alkyl radical, $R_{14}$, $R_{15}$, $R_{17}$ and $R_{18}$, which may be identical or different, represent, independently of one another, a hydrogen atom, a hydroxyl radical or a $C_1$-$C_4$ alkoxy radical, and also the tautomeric and/or mesomeric forms thereof, the stereoisomers thereof, the addition salts thereof with a cosmetically acceptable acid or base, and the hydrates thereof.

As regards the compounds of formula (I) as defined above, they can be in two tautomeric forms denoted (Ia) and (Ib):

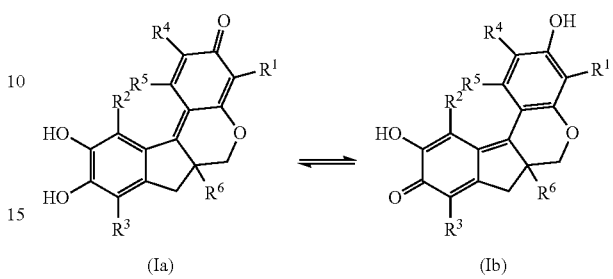

The alkyl radicals cited in the previous definitions of the substituents are linear or branched, saturated, generally $C_1$-$C_{20}$, particularly $C_1$-$C_{10}$, preferably $C_1$-$C_6$, hydrocarbon-based radicals, such as methyl, ethyl, propyl, butyl, pentyl and hexyl.

The alkoxy radicals are alkyloxy radicals with the alkyl radicals as defined above, and preferably the alkoxy radicals are $C_1$-$C_{10}$, such as methoxy, ethoxy, propoxy and butoxy.

When the alkyl or alkoxy radicals are substituted, they can be done so with at least one substituent borne by at least one carbon atom, chosen from:
 a halogen atom;
 a hydroxyl group;
 a $C_1$-$C_2$ alkoxy radical;
 a $C_1$-$C_{10}$ alkoxycarbonyl radical;
 a (poly)-($C_2$-$C_4$)hydroxyalkoxy radical;
 an amino radical;
 a 5- or 6-membered heterocycloalkyl radical;
 a 5- or 6-membered heteroaryl radical which is optionally cationic, preferably imidazolium, and optionally substituted with a ($C_1$-$C_4$)alkyl radical, preferably methyl;
 an amino radical substituted with one or two $C_1$-$C_6$ alkyl radicals, which may be identical or different, optionally bearing at least:
  one hydroxyl group,
  one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom other than or the same as nitrogen,
  one quaternary ammonium group —$N^+R'R''R'''$, $M^-$ for which R', R" and R"', which may be identical or different, represent a hydrogen atom, or a $C_1$-$C_4$ alkyl group; and $M^-$ represents the counterion of the corresponding organic acid, inorganic acid or halide,
  or one 5- or 6-membered heteroaryl radical which is optionally cationic, preferably imidazolium, and optionally substituted with a ($C_1$-$C_4$)alkyl radical, preferably methyl;
 an acylamino radical (—NR—COR') in which the R radical is a hydrogen atom or a $C_1$-$C_4$ alkyl radical optionally bearing at least one hydroxyl group, and the R' radical is a $C_1$-$C_2$ alkyl radical;
 a carbamoyl radical (($R)_2N$—CO—) in which the R radicals, which may be identical or different, represent a hydrogen atom or a $C_1$-$C_4$ alkyl radical optionally bearing at least one hydroxyl group;
 an alkylsulphonylamino radical ($R'SO_2$—NR—) in which the R radical represents a hydrogen atom or a $C_1$-$C_4$ alkyl radical optionally bearing at least one hydroxyl group, and the R' radical represents a $C_1$-$C_4$ alkyl radical or a phenyl radical;

an amino sulphonyl radical (($R)_2N$—$SO_2$—) in which the R radicals, which may be identical or different, represent a hydrogen atom or a $C_1$-$C_4$ alkyl radical optionally bearing at least one hydroxyl group;

a carboxylic radical in acid form or salified form (preferably salified with an alkali metal or a substituted or unsubstituted ammonium);

a cyano group;

a nitro group;

a carboxyl or glycosylcarbonyl group;

a phenylcarbonyloxy group optionally substituted with one or more hydroxyl groups;

a glycosyloxy group; and a phenyl group optionally substituted with one or more hydroxyl groups.

The term "glycosyl radical" is intended to mean a radical derived from a monosaccharide or polysaccharide.

Preferably, the alkyl or alkoxy radicals of formula (I) are not substituted.

According to one particular embodiment of the invention, the compounds of formula (I) comprise an $R^6$ radical representing a hydroxyl group.

Another particular embodiment of the invention concerns the compounds of formula (I), for which the $R^1$ radical represents a hydrogen atom or a hydroxyl group.

More particularly, the process for dyeing keratin fibres uses, in composition i), one or more dyes of formula (I) chosen from haematoxylin, haematein, brazilin and brazilein.

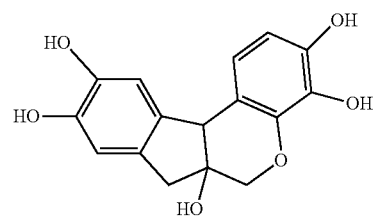

Haematoxylin (Natural Black 1-CAS 517-28-2)

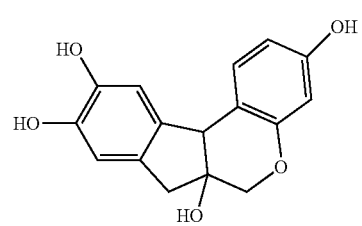

Brazilin (Natural Red 24-CAS 474-07-7)

Brazilein is a conjugated form of a chromane compound of formula A2. The scheme below contains the tautomeric structures (Ia) and (Ib) illustrated above.

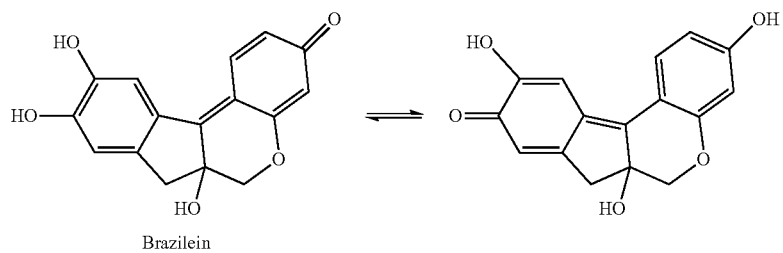

Brazilein

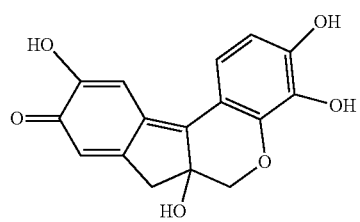

Haematein (oxidized form)

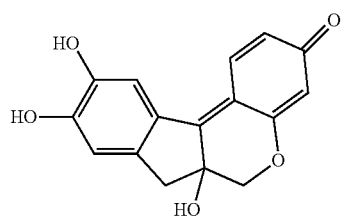

Brazilein (oxidized form)

Among the haematoxylin/haematein and brazilin/brazilein compounds, mention may be made, by way of example, of haematoxylin (Natural Black 1 according to the INCI name) and brazilin (Natural Red 24 according to the INCI name), compounds from the family of indochromanes, which are commercially available. The latter may exist in an oxidized form and be obtained by synthesis processes or by processes for extraction from plants or vegetables known to be rich in these compounds.

The compounds of formula (I) can be used in the form of extracts. Use may be made of the following plant extracts (genus and species): *Haematoxylon campechianum*, *Haematoxylon brasiletto*, *Caesalpinia echinata*, *Caesalpinia sappan*, *Caesalpinia spinosa* and *Caesalpina brasiliensis*.

The extracts are obtained by extraction of various parts of plants, such as, for example, the root, wood, bark or leaf.

According to one particular embodiment of the invention, the natural compounds of formula (I) are derived from logwood, pernambuco wood, sappan wood or brazilwood.

With regard to the compounds of formula (II), the compounds used in the present invention are preferably those for which $R_{11}$ and $R_{13}$ represent an alkyl radical, preferably methyl.

Preferably, $R_{12}$, $R_{16}$, $R_{19}$ and $R_{20}$ denote, independently of one another, a hydrogen atom or an alkyl radical, preferably methyl.

Preferably, $R_{14}$ and $R_{17}$ denote, independently of one another, a hydrogen atom or an alkoxy radical, preferably methoxy.

Preferably, $R_{18}$ and $R_{15}$ denote, independently of one another, a hydrogen atom, a hydroxyl radical or an alkoxy radical, preferably methoxy.

A first particularly preferred family of compounds suitable for the present invention is that of the compounds corresponding to formula (II) above for which $R_{12}$, $R_{15}$, $R_{16}$, $R_{17}$, $R_{19}$ and $R_{20}$ each represent a hydrogen atom, $R_{11}$ and $R_{13}$ each represent a methyl radical and $R_{14}$ represents a methoxy radical.

Among the preferred compounds of this first family are those for which $R_{18}$ represents a methoxy radical (santalin B) or a hydroxyl radical (santalin A).

A second particularly preferred family of compounds suitable for the present invention is that of the compounds corresponding to formula (II) above for which:

$R_{11}$ and $R_{13}$ each represent a methyl radical, $R_{17}$ represents the methoxy radical.

A preferred compound of this second family is that for which, in addition, $R_{19}$ represents a methyl radical, $R_{20}$, $R_{12}$, $R_{14}$, $R_{18}$ and $R_{16}$ each represent a hydrogen atom, and $R_{15}$ represents the hydroxyl radical (santarubin A).

A second preferred compound of this second family is that for which $R_{18}$, $R_{20}$, $R_{12}$, $R_{14}$ and $R_{16}$ represent a hydrogen atom, $R_{15}$ represents a methoxy radical and $R_{19}$ represents a methyl radical (santarubin B).

A third preferred compound of this second family is that for which $R_{20}$, $R_{12}$, $R_{14}$, $R_{15}$, $R_{16}$ and $R_{19}$ represent hydrogen and $R_{18}$ represents the hydroxyl radical (santarubin C).

Another preferred compound of this second family is that for which $R_{15}$ represents a methoxy radical, $R_{18}$ and $R_{14}$ represent a hydrogen atom, and $R_{20}$, $R_{12}$, $R_{16}$ and $R_{19}$ represent a methyl radical (tetra-O-methyl-cantarubin).

The compounds of formula (II) can be used in the form of extracts. Use may be made of plant extracts of red woods, generally grouping together the Asian and West African red wood species of the *Pterocarpus* genus and of the *Baphia* genus. These woods are, for example, *Pterocarpus santalinus, Pterocarpus osun, Pterocarpus soyauxii, Pterocarpus erinaceus, Pterocarpus indicus* or else *Baphia nitida*. These woods can also be called padauk, sandalwood, narra wood, camwood or else barwood.

Thus, extracts, containing compounds of formula (II), that can be used in the present invention can, for example, be obtained from red sandalwood (*Pterocarpus santalinus*), by aqueous basic extraction, such as the product sold under the trade name Santal Concentré SL 709C by the company Copiaa, or else by means of solvent extraction of sandalwood powder, such as the product sold under the trade name Santal Poudre SL PP by the same company Copiaa. Mention may also be made of the aqueous-alcoholic extract of red sandalwood powder from the company Alban Muller.

Extracts which are also suitable for the present invention can be obtained from woods such as camwood (*Baphia nitida*) or else barwood (*Pterocarpus soyauxii, Pterocarpus erinaceus*): the latter is thus fractionated and then milled: a conventional alcoholic extraction or an extraction by percolation is then carried out on this milled material in order to collect a pulverulent extract which is particularly suitable for the implementation of the present invention.

The salts of the compounds of formulae (I) and (II) of the invention can be salts of cosmetically acceptable acids or bases.

The acids may be mineral or organic. Preferably, the acid is hydrochloric acid, resulting in chlorides.

The bases may be mineral or organic. In particular, the bases are alkali metal hydroxides such as sodium hydroxide, resulting in sodium salts.

Preferably, the compound(s) of formulae (I) and (II) used in the process according to the invention are derived from plant extracts. Mixtures of plant extracts can also be used.

The natural extracts according to the invention can be in the form of powders or liquids. Preferably, the extracts of the invention are in the form of a powder.

Preferably, the chromene or chromane dyes used are chosen from haematein, haematoxylin, brazilein, brazilin and santalin A. Even more preferentially, use is preferably made of the dyes of formula (I), and most particularly haematein and brazilein.

Preferably, the process according to the invention uses a composition containing from 0.001% to 20% by weight of dyes chosen from chromene dyes and chromane dyes, relative to the total weight of the final composition containing them, preferably from 0.01% to 10% by weight. The term "final composition" is intended to mean the composition ready to be applied to the keratin fibres, i.e. either composition i) as defined above, or a composition resulting from the mixing of composition i) and composition ii).

The process according to the invention also uses a composition comprising one or more zinc (Zn) mineral salts.

For the purpose of the present invention, the term "mineral salts" is intended to mean inorganic salts, i.e. which do not comprise in their structure a carbon atom linked to at least one hydrogen atom. The mineral salts are salts derived from the action of a mineral acid or of a mineral base on zinc.

Among the salts, mention may be made of the halides, such as chlorides, fluorides and iodides; the sulphates, the phosphates, the nitrates and the carbonates, and also mixtures thereof.

Preferably, the zinc salts used are zinc sulphate and zinc chloride.

The zinc salts can be introduced in solid form into the compositions, or else can originate from a natural, mineral or spring water rich in these ions or else from seawater (Dead Sea, in particular). They can also originate from mineral compounds, for instance earths, rocks, ochres such as clays (green clay, for example), or even from a plant extract containing them, as described, for example, in document FR 2 814 943.

By way of mineral rock containing zinc salts, mention may be made of the following rocks:

| | |
|---|---|
| Boyleite | $(ZnMg)SO_4$—$4H_2O$ |
| Changoite | $Na_2Zn(SO_4)_2$—$4H_2O$ |
| Clinohedrite | $CaZn[SiO_4]$—$H_2O$ |
| Gaultite | $Na_4Zn_2Si_7O_{18}$—$5H_2O$ |
| Goslarite | $ZnSO_4$—$7H_2O$ |
| Hardystonite | $Ca_2Zn[Si_2O_7]$ |
| Hopeite | $Zn_3(PO_4)_2$—$4H_2O$ |
| Hydrozincite | $Zn_5[(OH)_3|CO_3]_2$ |
| IMA2008-048 | $Zn_6(PO_4)_4$—$7H_2O$ |
| Minrecordite | $CaZn(CO_3)_2$ |
| Osakaite | $Zn_4(SO_4XOH)_6$—$5H_2O$ |
| Parahopeite | $Zn_3(PO_4)_2$—$4H_2O$ |
| Parascholzite | $CaZn_2(PO_4)_2$—$2H_2O$ |
| Scholzite | $CaZn_2(PO_4)_2$—$2H_2O$ |
| Simonkolleite | $Zn_5[(OH)_8|Cl_2]$—$H_2O$ |
| Skorpionite | $Ca_3Zn_2[(OH)_2|CO_3|(PO_4)_2]$—$H_2O$ |
| Smithsonite | $ZnCO_3$ |
| Spencerite | $Zn_4[OH|PO_4]_2$—$3H_2O$ |
| Tarbuttite | $Zn_2[OH|PO_4]$ |
| Basic Zinc Sulphate Hydrate | $Zn_4SO_4(OH)_6$—$4H_2O$ |
| Willemite | $Zn_2[SiO_4]$ |

| | -continued |
|---|---|
| Zincsilite | $Zn_3Si_4O_{10}(OH)_2$—$4H_2O$ |
| Zinkosite | $ZnSO_4$ |

In particular, the zinc salts of the invention are in oxidation state 2: Zn(II).

Preferably, the process according to the invention uses a composition containing from 0.001% to 20% by weight of zinc mineral salts, relative to the total weight of the final composition containing them, preferably from 0.05 to 10% by weight. The term "final composition" is intended to mean the composition ready to be applied to the keratin fibres, i.e. either composition ii) as defined above, or a composition resulting from the mixing of composition ii) and composition i).

The compounds present in compositions i) and ii) as defined above and used in the process according to the invention are in one or more cosmetic compositions which may, independently of one another, be in various galenical forms, such as a powder, a lotion, a foam, a cream or a gel or any other form suitable for carrying out dyeing of keratin fibres. They can also be packaged in a pump dispenser without propellant or pressurized in an aerosol container in the presence of a propellant and form a foam.

The compositions used in the process according to the invention comprise a medium suitable for dyeing, also known as dyeing vehicle, which can contain water, a mixture of water and one or more organic solvents or else a mixture of organic solvents, when the composition is in liquid form.

According to one particular embodiment of the invention, the cosmetic composition(s) according to the invention contain(s) water.

By way of organic solvent, mention may, for example, be made of $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether, diethylene glycol monomethyl ether, and hexylene glycol.

The organic solvents are present in proportions preferably of between 1% and 40% by weight approximately, relative to the total weight of the final dye composition, and even more preferably between 5% and 30% by weight approximately.

According to another embodiment of the invention, at least one of the compositions used in the process of the invention is anhydrous and can be in pulverulent or pasty form.

When the composition is in pulverulent form, it can contain pulverulent ingredients other than the compounds present in compositions i) and ii).

When the composition is in the form of a paste, it can optionally contain one or more inert organic liquids, preferably chosen from liquid petroleum jelly, polydecenes and fatty esters which are liquid at ambient temperature (25° C.) and at atmospheric pressure (760 mmHg, i.e. 1.013 bar).

When the process uses a single composition containing the compounds of compositions i) and ii) and this composition is anhydrous, the locks of hair to which the composition will be applied are wetted beforehand.

The process according to the invention should not comprise any chemical oxidizing agent other than the oxygen in the air.

The term "chemical oxidizing agent" denotes hydrogen peroxide, urea peroxide, alkali metal bromates, and persalts such as perborates and persulphates.

The compositions used in the dyeing process in accordance with the invention can also contain various adjuvants conventionally used in compositions for dyeing the hair, such as anionic, cationic, non-ionic, amphoteric or zwitterionic surfactants or mixtures thereof, anionic, cationic, non-ionic, amphoteric or zwitterionic polymers or blends thereof, inorganic or organic thickeners, and in particular anionic, cationic, non-ionic and amphoteric polymeric associative thickeners, antioxidants, penetration agents, sequestrants, fragrances, buffers, dispersants, conditioning agents such as, for example, volatile or non-volatile and modified or unmodified silicones, film-forming agents, ceramides, preservatives or opacifiers.

Said adjuvants are preferably chosen from surfactants, such as anionic or non-ionic surfactants or mixtures thereof, and inorganic or organic thickeners.

The above adjuvants are generally present in an amount of, for each of them, between 0.01% and 40% by weight, relative to the weight of the composition, preferably between 0.1% and 20% by weight, relative to the weight of the composition(s) used.

Of course, a person skilled in the art will take care to select this or these optional additional compounds in such a way that the advantageous properties intrinsically attached to the composition(s) of use in the dyeing process in accordance with the invention are not, or not substantially, impaired by the addition(s) envisaged.

The process according to the invention can use one or more additional direct dyes, it being possible for the latter to be contained in composition(s) i) and ii).

These direct dyes are, for example, chosen from those conventionally used in direct dyeing, and among which mention may be made of all the aromatic and/or nonaromatic dyes commonly used, such as neutral, acidic or cationic nitrobenzene direct dyes, neutral, acidic or cationic azo direct dyes, natural direct dyes other than ortho-diphenols, quinone direct dyes and in particular neutral, acidic or cationic anthraquinone direct dyes, azine, triarylmethane or indoamine direct dyes, methines, styryls, porphyrins, metalloporphyrins, phthalocyanines, methinecyanines and fluorescent dyes.

Among the natural direct dyes, mention may be made of lawsone, juglone, indigo, isatin, curcumin, spinulosin, apigenidine or orceins. Use may also be made of extracts or decoctions containing these natural dyes, and in particular henna-based extracts or cataplasms.

The additional direct dye(s) in the composition(s) of the dyeing process according to the invention, or of the composition according to the invention, preferably represent from 0.001% to 10% by weight approximately of the total weight of the composition(s) used.

When the chromene and/or chromane dye(s) is (are) in an aqueous composition, the pH of this aqueous dye composition is between 2 and 12, and is preferably greater than 7, and even more preferably between 8 and 12, and particularly between 8 and 10.

This pH can be adjusted to the desired value by means of acidifying or basifying agents commonly used in the dyeing of keratin fibres or else using conventional buffer systems.

Among the acidifying agents of the compositions used in the invention, mention may, for example, be made of mineral or organic acids such as hydrochloric acid, orthophosphoric acid or sulphuric acid, carboxylic acids such as acetic acid, tartaric acid, citric acid or lactic acid, and sulphonic acids.

More particularly, this basic agent is chosen from aqueous ammonia, alkali metal carbonates, alkanolamines, such as mono-, di- and triethanolamines, and also derivatives thereof, sodium hydroxide or potassium hydroxide and the compounds of formula (III) below:

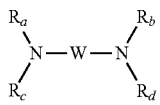

(III)

in which formula (III), W is a propylene residue optionally substituted with a hydroxyl group or a $C_1$-$C_4$ alkyl radical; and $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

According to a first particular embodiment of the invention, the dyeing process is carried out in one step, by application to the keratin fibres of a cosmetic dye composition containing the following ingredients:
  one or more dyes chosen from chromene dyes and chromane dyes,
  one or more zinc mineral salts,
said process excluding any use of a chemical oxidizing agent other than the oxygen in the air.

The cosmetic composition defined above can be applied as it is to the keratin fibres. It can also be ready-to-use and result from extemporaneous mixing of at least two compositions, which may be provided in a dyeing kit.

Advantageously, at least one of said compositions containing, together or separately, the ingredients is aqueous.

The leave-in time is generally fixed between 3 and 120 minutes, preferably between 10 and 60 minutes, and more preferably between 15 and 45 minutes.

According to a second particular embodiment of the invention, the dyeing process is carried out, in several steps, by application to the keratin fibres of several cosmetic dye compositions containing, together or separately, in said composition(s), the following ingredients:
  one or more dyes chosen from chromene dyes and chromane dyes,
  one or more zinc mineral salts,
said process excluding any use of a chemical oxidizing agent other than the oxygen in air. These steps can be optionally separated by intermediate rinsing. In the absence of such intermediate rinsing, wringing-out with a towel or paper can be carried out in order to remove the surplus composition.

In a first variant of a two-step process, the first step consists in applying to said fibres a cosmetic composition i) comprising one or more dyes chosen from the chromene dyes and the chromane dyes as defined above, and then a second step consists in applying to said fibres a cosmetic composition ii) comprising one or more zinc mineral salts as defined above.

In a second variant of a two-step process for dyeing keratin fibres, the first step consists in applying to said fibres a composition ii) comprising one or more zinc mineral salts as defined above, and then a second step consists in applying to said fibres a second cosmetic composition i) comprising one or more dyes chosen from the chromene dyes and the chromane dyes as defined above.

For the latter two processes, the leave-in time after application of the cosmetic composition for the first step is generally fixed between 3 and 120 minutes, preferably between 10 and 60 minutes, and more preferably between 15 and 45 minutes. The leave-in time after application of the second cosmetic composition for the second step is generally fixed between 3 and 120 minutes, preferably between 3 and 60 minutes, and more preferably between 5 and 30 minutes.

Irrespective of the mode of application, the application temperature is generally between ambient temperature (15 to 25° C.) and 80° C., and more particularly between 15 and 45° C. Thus, it is advantageously possible, after application of the composition according to the invention, to subject the head of hair to a heat treatment by heating at a temperature of between 30 and 60° C. In practice, this operation can be carried out using a hairstyling hood, a hair dryer, a dispenser of infrared rays and other conventional heating devices.

Use may also be made, both as means for heating and for smoothing the head of hair, of a heating iron at a temperature of between 60 and 220° C., and preferably between 120 and 200° C.

The invention also relates to a cosmetic dye composition comprising:
  one or more dyes chosen from chromene dyes and chromane dyes, as defined above,
  one or more zinc mineral salts, as defined above, and
  one or more organic solvents which are liquid at a temperature of 25° C. and at atmospheric pressure (760 mmHg, i.e. 1.013 bar) and which have a value for the Hansen parameter δH at 25° C. and at atmospheric pressure (760 mmHg, i.e. 1.013 bar) of less than 15, preferably of between 0 and 14, and even more preferably between 4 and 10.

The organic solvent(s) which has (have) a Hansen solubility parameter δH value as defined above are, for example, described in the reference handbook "Hansen solubility parameters. A user's handbook, Charles M. HANSEN", CRC Press, 2000, pages 167 to 185.

This value takes into account the δH solubility parameter linked to the formation of hydrogen bonds. It may be recalled that three major types of interactions exist in organic compounds: nonpolar interactions, permanent dipole-dipole interactions and interactions of hydrogen bond type, the latter being the subject of the parameter defining the organic solvent in the present invention.

By way of examples of solvents which meet this definition, mention may be made of propylene glycol derivatives, alkylene carbonates, benzyl alcohol, and mixtures thereof.

In particular, mention may be made of the following compounds:

| Name | Chemical formula | δH |
|---|---|---|
| Dipropylene glycol methyl ether | $CH_3O[CH_2CH(CH_3)O]_2H$ | 11.2 |
| Tripropylene glycol methyl ether | $CH_3O[CH_2CH(CH_3)O]_3H$ | 10.4 |
| Propylene glycol n-butyl ether (PnB) | $C_4H_9OCH_2CH(CH_3)OH$ | 9.2 |
| Propylene glycol n-propyl ether (PnP) | $C_9H_7OCH_2CH(CH_3)OH$ | 9.2 |
| Dipropylene glycol monomethyl ether acetate | $CH_3COO[CH_2CH(CH_3)O]_2CH_3$ | 8.0 |
| Benzyl alcohol | $C_6H_5CH_2OH$ | 13.7 |
| Ethylene glycol 2-ethylhexyl ether | $C_8H_{17}OCH_2CH_2OH$ | 5.1 |
| 2-pentanol | $CH_3CH(OH)C_3H_7$ | 13.3 |

By way of alkylene carbonate, mention may be made of the compounds having the following chemical formula:

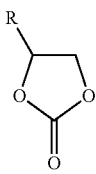

in which R=H, $C_1$-$C_8$ alkyl or $C_1$-$C_4$ hydroxyalkyl.

By way of example, mention may be made of ethylene carbonate (R=H), propylene carbonate (R=$CH_3$), glyceryl carbonate (R=$CH_2OH$), or else butylene carbonate (R=$CH_2CH_3$). Among the alkylene carbonates of the invention, propylene carbonate is preferred.

According to one particular embodiment, the δH value is preferably less than 14, preferably less than 12, and better still less than 10. According to one particularly preferred embodiment, the value of the δH component is greater than 0. According to one variant, the value of δH is greater than 3, preferably greater than 4.

The composition of the invention generally comprises an amount of organic solvents which have a Hansen SH parameter of less than 15 of between 0.1% and 80%, preferably between 0.5% and 50%, and even more preferably between 1% and 30%, of the total weight of the composition.

Of course, the composition according to the invention can be used according to the process according to the invention as defined above and can comprise the additional compounds, such as, inter alia, the direct dyes, mentioned above for compositions i) and ii).

The invention also relates to the use of the composition according to the invention, for dyeing keratin fibres, such as human keratin fibres, and in particular the hair.

A kit or device can be used for carrying out the process according to the invention. The kit can comprise at least two compartments:

a first compartment comprising a cosmetic composition i) containing one or more dyes chosen from the chromene dyes and the chromane dyes as defined in any one of claims 1 to 5, and a second compartment comprising a cosmetic composition ii) containing one or more zinc mineral salts as defined in any one of claims 1, 6 and 7.

According to one variant, the kit also comprises an additional composition comprising one or more treating agents.

The compositions of the kit are packaged in separate compartments, optionally accompanied by suitable application means, which may be identical or different, such as fine brushes, brushes or sponges.

The kit mentioned above can also be equipped with a means for delivering the desired mixture onto the hair, for example such as the devices described in patent FR 2 586 913.

DYEING EXAMPLES

1/ Preparation of the Compositions
1. Zinc Compositions
Zinc compositions are prepared: solutions, at 1% with respect to zinc element, of each of the following zinc compounds:

| Zinc compound used | |
|---|---|
| 1 (invention) | Zinc sulphate heptahydrate |
| 2 (comparative) | Zinc acetate |

2. Dye Compositions
The following dyeing composition is also prepared from the following ingredients in the following proportions indicated as % by weight of active material:

| | |
|---|---|
| Propylene carbonate | 10% |
| Benzyl alcohol | 2.5% |
| Ethanol | 5% |
| Hydroxyethylcellulose | 2% |
| Haematein** | 2% |
| pH agent | qs pH = 7 |
| Fragrance | qs |
| Water | qs 100% |

**Haematein, CAS = 475-25-2, sold under the reference 51230 by Fluka.

2/ Application of the Compositions
Two series of tests are carried out: one on locks of hair containing 90% of natural white hairs; the other on locks of permanent-waved hair. The locks of hair are successively treated in a proportion of 5 g of composition per g of lock according to the following process:

1. application to said locks of hair of the aqueous composition containing the zinc salt for 10 minutes at ambient temperature (22° C.),
2. wringing-out of the treated locks,
3. application of the dyeing composition, for 45 minutes at 40° C.

After the application of these treatments, the locks are rinsed, shampooed and dried.

3/ Evaluation of the Treated Locks
The following results of dyeing on locks are obtained:

| | Natural hair | Permanent-waved hair | Selectivity |
|---|---|---|---|
| No zinc pretreatment (comparative) | pearlescent coppery | coppery | selective |
| Treatment with zinc sulphate (treatment 1) according to the invention | vivid purple | vivid purple | not very selective |
| Comparative treatment with zinc acetate (treatment 2) | vivid mahogany | purple | very selective |

The selectivity expresses the difference in colour between a natural hair and a permanent-waved hair. The greater the selectivity, the greater the difference in colour between the dyed locks of natural hair and the dyes locks of permanent-waved hair.

It is noted that the process of the invention makes it possible to dye the hair a vivid colour which is not very selective, since the highlight remains similar between that of the natural hair and that of the permanent-waved hair.

This is not the case with the dyeing process using an organic zinc compound such as zinc acetate.

A series of 10 washes applied to the two types of locks treated according to the process according to the invention and with the composition according to the invention causes only a weak degradation of the colouration.

Example 2

1/ Preparation of the Dye Composition
The following dyeing composition is prepared from the following ingredients in the following proportions indicated as % by weight of active material:

| Dyeing product | |
|---|---|
| | A |
| Haematein [1] | 1% |
| Chlorophyllin [2] | 0.19% |
| Curcumin [3] | 0.58% |
| *Sorghum* | 0.34% |
| Ethanol | 15% |
| Benzyl alcohol | 4% |
| Benzoic acid | 0.2 |
| pH agent | qs pH = 8.8 |
| Fragrance | qs |
| Water | qs 100% |

[1] Haematein, CAS = 475-25-2, sold under the reference 51230 by Fluka
[2] Dye E 141
[3] Dye E100

2/ Application of the Compositions

Pairs of locks of natural and permanent-waved hair containing 90% white hairs are treated for 10 minutes at ambient temperature with a zinc phosphate composition at 1 g % with respect to zinc element.

They are then treated for 30 minutes at a temperature of 40° C. with composition A. They are then rinsed, shampooed and dried.

Locks powerfully dyed black are obtained.

3/ Evaluation of the Treated Locks

These results are accompanied by colorimetric measurements given in the following table:

| | Rise on natural hair | | | | Rise on permanent-waved hair | | | |
|---|---|---|---|---|---|---|---|---|
| | L* | a* | b* | ΔE/non-dyed hair | L* | a* | b* | ΔE/non-dyed hair |
| Non-dyed hair | 63.44 | 0.99 | 13.03 | — | 63.91 | 1.25 | 13.56 | — |
| Hair dyed according to the invention | 20.72 | 4.59 | 0.34 | 44.7 | 20.96 | 2.57 | -0.38 | 45.18 |

A portion of these locks are then subjected to:
- a test of fastness in response to 5 or 10 shampooing operations with a commercial Elsève multivitamin 2-in-1 shampoo (brand l'Oreal Paris), or
- a test of fastness in response to light/UV after 18 h in an Atlas Suntest XLS+.

The colour of the locks was evaluated before and after exposure to light in the L* a* b* system, by means of a Minolta® CM 2600D spectrophotometer (Illuminant D65). In this L* a* b* system, L* represents the intensity of the colour, a* indicates the green/red colour axis and b* the blue/yellow colour axis. The lower the value of L, the darker or more intense the colour. The higher the value of a*, the redder the shade and the higher the value of b*, the bluer the shade.

The variation in the colouration of the locks before and after exposure to light is measured by (AE) according to the following equation:

$$\Delta E = \sqrt{(L^* - L_o^*)^2 + (a^* - a_o^*)^2 + (b^* - b_o^*)^2}$$

In this equation, L*, a* and b* represent the values measured after exposure to light and L0*, a0* and b0* represent the values measured before exposure.

The higher the value of AE, the greater the difference in colour of the lock before and after exposure, which shows a lesser light-fastness.

The colour degradation results are then expressed in ΔE (after test/before test) and given in the following table:

| | Colour degradation on natural hair | | | Colour degradation on permanent-waved hair | | |
|---|---|---|---|---|---|---|
| A | ΔE after light/UV exposure | ΔE after 5 shampooing operations | ΔE after 10 shampooing operations | ΔE after light/UV exposure | ΔE after 5 shampooing operations | ΔE after 10 shampooing operations |
| Hair dyed according to the invention | 3.80 | 2.45 | 3.72 | 0.5 | 1.5 | 3.10 |

It is noted that composition A of the invention results in a colouration which exhibits a very good level of fastness after shampooing operations and exposure to light and to UV radiation.

Example 3

1/ Preparation of the Dye Composition

The following dyeing compositions are prepared from the following ingredients in the following proportions indicated as % by weight of active material:

| Dyeing gel | | | | |
|---|---|---|---|---|
| | B | C | D | E |
| Haematein [1] | 0.3% | 0.3% | 0.3% | 0.3% |
| Curcumin [2] | 0.5% | 0.5% | 0.5% | 0.5% |
| Chlorophyllin [3] | 0.15% | 0.15% | 0.15% | 0.15% |
| *Sorghum* | 0.02% | 0.02% | 0.02% | 0.02% |
| Laccaic acid | 0.01% | 0.01% | 0.01% | 0.01% |
| Ethanol | 15% | 16% | 15% | 10% |
| Benzyl alcohol | 5% | 1% | — | — |
| 3-phenyl-1-propanol | — | 0.5% | — | — |
| 2-phenyl-1-ethanol | — | 1% | — | — |
| Benzoic acid | 0.5 | 0.5% am | — | — |
| Decanol | — | — | 5% | — |
| Sodium lauryl sulphate | — | — | 2% | 2% |
| Hydroxyethylcellulose (MW: 720,000) [4] | 2% | 2% | 2% | 2% |
| pH agent | qs pH = 8.8 | qs pH = 8.8 | qs pH = 8.8 | qs pH = 8.8 |
| Fragrance | qs | qs | qs | qs |
| Water | qs 100% | qs 100% | qs 100% | qsp100% |

[1] Haematein, CAS = 475-25-2, sold under the reference 51230 by Fluka
[2] Dye E100
[3] Dye E 141
[4] NATROSOL 250 MR from Aqualon 2/ Application of the Compositions Pairs of locks of natural and permanent-waved hair containing 90% white hairs are treated for 10 minutes at ambient temperature with a zinc phosphate composition at 1 g% with respect to zinc element.

The locks are then treated for 30 minutes at a temperature of 40° C. with compositions B to E. They are then rinsed, shampooed and dried.

3/ Evaluation of the Treated Locks

Colourations resistant to shampooing operations and UV radiation are obtained.

The invention claimed is:

1. Process for dyeing keratin fibres, such as human keratin fibres, and in particular the hair, comprising the application, to said fibres, of:
   i) a composition comprising one or more dyes chosen from chromene dyes and chromane dyes, ii) a composition comprising one or more zinc mineral salts, the compositions i) and ii) being two distinct compositions or forming a single composition, said process excluding any use of a chemical oxidizing agent other than the oxygen in the air.

2. Dyeing process according to claim 1, characterized in that the dye is chosen from the compounds having the following formulae:

formula (I):

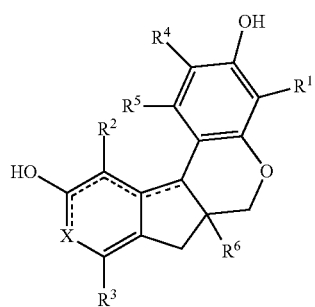

in which:
---- represents a carbon-carbon single bond or a carbon-carbon double bond, the linking of these bonds
==== denotes two carbon-carbon single bonds and two carbon-carbon double bonds, said bonds being conjugated, X represents a group:

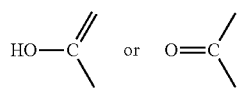

R1, R2, R3, R4, R5 and R6, which may be identical or different, represent, independently of one another, a hydrogen atom, a hydroxyl group, an optionally substituted alkyl group, an optionally substituted alkoxy group or an optionally substituted acyloxy group, and also the tautomeric and/or mesomeric forms thereof, the stereoisomers thereof, the addition salts thereof with a cosmetically acceptable acid or base, and the hydrates thereof; and formula (II):

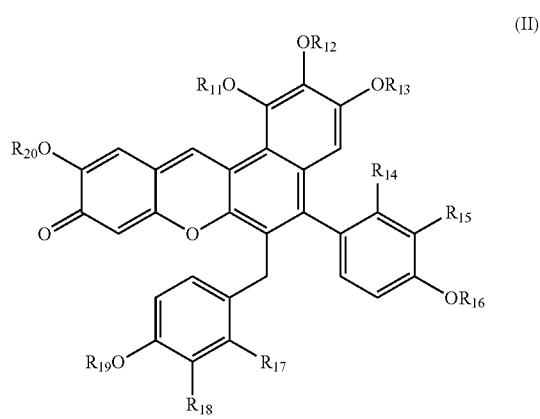

in which:
R11, R12, R13, R16, R19 and R20, which may be identical or different, represent, independently of one another, a hydrogen atom or a C1-C4 alkyl radical, R14, R15, R17 and R18, which may be identical or different, represent, independently of one another, a hydrogen atom, a hydroxyl radical or a C1 C4 alkoxy radical, and also the tautomeric and/or mesomeric forms thereof, the stereoisomers thereof, the addition salts thereof with a cosmetically acceptable acid or base, and the hydrates thereof.

3. Dyeing process according to claim 1, characterized in that the dye present in composition i) is chosen from haematoxylin, brazilin, haematein, brazilein, santalins and santarubins, and the tautomeric and/or mesomeric forms thereof, the stereoisomers thereof, the addition salts thereof with a cosmetically acceptable acid or base, and also the hydrates.

4. Dyeing process according to claim 1, characterized in that the dye present in composition i) is chosen from haematein and brazilein having the following structure:

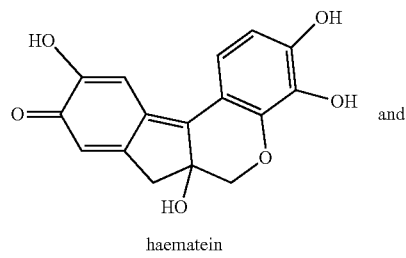

haematein

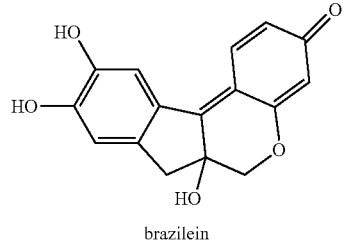

brazilein and the tautomeric and/or mesomeric forms thereof, the stereoisomers thereof, the addition salts thereof with a cosmetically acceptable acid or base, and also the hydrates.

5. Dyeing process according to claim 1, characterized in that the dye(s) i) is (are) present in the final composition containing it (them) in a content of between 0.001% and 20% by weight, relative to the total weight of the composition.

6. Dyeing process according to claim 1, characterized in that the zinc mineral salts are chosen from zinc halides, sulphates, phosphates, nitrates and carbonates and also mixtures thereof.

7. Dyeing process according to claim 6, characterized in that the zinc mineral salt(s) is (are) present in the final composition containing it (them) in a content of between 0.001% and 20% by weight, relative to the total weight of the composition.

8. Dyeing process according to claim 1, characterized in that it comprises a step consisting in applying to the keratin fibres a cosmetic composition comprising one or more dyes chosen from haematoxylin, brazilin, haematein, brazilein, santalins and santarubins, and the tautomeric and/or mesomeric forms thereof, the stereoisomers thereof, the addition salts thereof with a cosmetically acceptable acid or base, and also the hydrates, and one or more zinc mineral salts chosen from zinc halides, sulphates, phosphates, nitrates and carbonates and also mixtures thereof.

9. Dyeing process according to claim 1, characterized in that it comprises two steps consisting, in the first step, in applying to the keratin fibres a cosmetic composition i) comprising one or more dyes chosen from haematoxylin, brazilin, haematein, brazilein, santalins and santarubins, and the tautomeric and/or mesomeric forms thereof, the stereoisomers thereof, the addition salts thereof with a cosmetically acceptable acid or base, and also the hydrates, and then consisting, in a second step, in applying a cosmetic composition ii) comprising one or more zinc mineral salts chosen from zinc halides, sulphates, phosphates, nitrates and carbonates and also mixtures thereof.

10. Dyeing process according to claim 1, characterized in that it comprises two steps consisting, in the first step, in applying to the keratin fibres a composition ii) comprising one or more zinc mineral salts chosen from zinc halides, sulphates, phosphates, nitrates and carbonates and also mixtures thereof, and then consisting, in a second step, in applying a composition i) comprising one or more dyes chosen from haematoxylin, brazilin, haematein, brazilein, santalins and santarubins, and the tautomeric and/or mesomeric forms thereof, the stereoisomers thereof, the addition salts thereof with a cosmetically acceptable acid or base, and also the hydrates.

11. Cosmetic dyeing composition comprising:
one or more dyes chosen from haematoxylin, brazilin, haematein, brazilein, santalins and santarubins, and the tautomeric and/or mesomeric forms thereof, the stereoisomers thereof, the addition salts thereof with a cosmetically acceptable acid or base, and also the hydrates,
one or more zinc mineral salts chosen from zinc halides, sulphates, phosphates, nitrates and carbonates and also mixtures thereof, and
one or more organic solvents which are liquid at a temperature of 25° C. and at atmospheric pressure (760 mmHg, i.e. 1.013 bar) and which have a value for the Hansen parameter δH at 25° C. and at atmospheric pressure of less than 15.

12. Composition according to claim 11, characterized in that the organic solvent is chosen from propylene glycol derivatives, alkylene carbonates, benzyl alcohol and mixtures thereof.

13. Process for dyeing keratin fibres, such as human keratin fibres, comprising the application of a cosmetic dye composition comprising:

one or more dyes chosen from haematein and brazilein having the following structure:

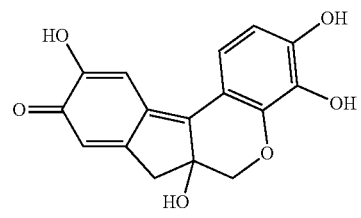
haematein and

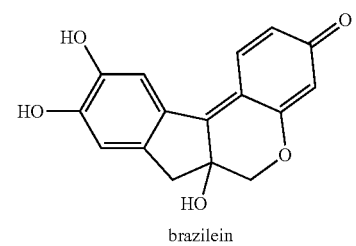
brazilein one or more zinc mineral salts chosen from zinc halides, sulphates, phosphates, nitrates and carbonates and also mixture thereof, and
one or more organic solvents which are liquid at the temperature of 25° C. and at atmospheric pressure (760 mmHg, i.e. 1.013 bar) and which have a value for the Hansen parameter δH at 25° C. and at atmospheric pressure of less than 15.

14. Kit comprising at least two compartments:
a first compartment comprising a cosmetic composition i) comprising one or more dyes chosen from haematein and brazilein having the following structure:

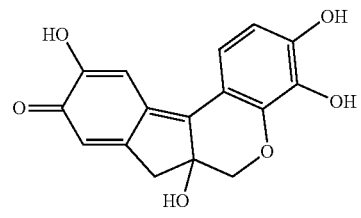
haematein and

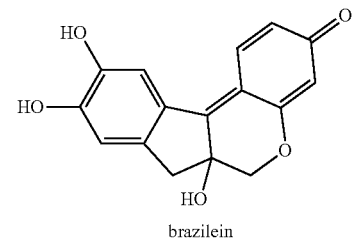
brazilein and the tautomeric and/or mesomeric forms thereof, the stereoisomers thereof, the addition salts thereof with a cosmetically acceptable acid or base, and also the hydrates, and
a second compartment comprising a cosmetic composition ii) containing one or more zinc mineral salts chosen from zinc halides, sulphates, phosphates, nitrates and carbonates and also mixtures thereof.

* * * * *